United States Patent [19]
Parker

[11] Patent Number: 6,144,868
[45] Date of Patent: Nov. 7, 2000

[54] REUSABLE PULSE OXIMETER PROBE AND DISPOSABLE BANDAGE APPARATUS

[75] Inventor: Brent Parker, Murrieta, Calif.

[73] Assignee: Sensidyne, Inc., Clearwater, Fla.

[21] Appl. No.: 09/289,647

[22] Filed: Apr. 12, 1999

Related U.S. Application Data

[60] Provisional application No. 60/104,332, Oct. 15, 1998.

[51] Int. Cl.[7] ................................................. A61B 5/00
[52] U.S. Cl. ............................................ 600/344; 600/310
[58] Field of Search ..................................... 600/310, 322, 600/323, 340, 344, 473, 476

[56] References Cited

U.S. PATENT DOCUMENTS

| Re. 36,000 | 12/1998 | Swedlow et al. . |
| 4,621,643 | 11/1986 | New, Jr. et al. . |
| 4,685,464 | 8/1987 | Goldberger et al. . |
| 4,700,708 | 10/1987 | New, Jr. et al. . |
| 4,830,014 | 5/1989 | Goodman et al. . |
| 5,090,410 | 2/1992 | Saper et al. . |
| 5,094,240 | 3/1992 | Muz . |
| 5,170,786 | 12/1992 | Thomas et al. . |
| 5,507,286 | 4/1996 | Solenberger . |
| 5,673,693 | 10/1997 | Solenberger . |
| 5,678,544 | 10/1997 | Delonzor et al. . |
| 5,817,010 | 10/1998 | Hibl . |
| 5,879,373 | 3/1999 | Röper et al. ............................ 600/344 |

*Primary Examiner*—Eric F. Winakur
*Attorney, Agent, or Firm*—Jim Zegeer

[57] ABSTRACT

A reusable pulse oximeter and disposable bandage apparatus and method which includes a reusable oximeter probe assembly with at least one light emitting diode, one photocell detector, each of which is enclosed in first and second plastic housings, respectively. A generally planar bandage strip having adhesive on at least a portion of at least one face thereof and at least two plastic receptacles attached to the other face thereof, each receptacle having an aperture and being adapted to matedly receive the first and second housings of the reusable pulse oximeter probe, respectively. In use the apertures are aligned on the digit of a patient by looking through the aperture in order to attach a first aperture over the nail bed of a patient and, subsequently, engaging the reusable probe components in the receptacles.

10 Claims, 4 Drawing Sheets 6,144,868

REUSABLE PULSE OXIMETER PROBE AND DISPOSABLE BANDAGE APPARATUS

REFERENCE TO RELATED APPLICATION

This application is the subject of provisional application Ser. No. 60/104,332 filed Oct. 15, 1998 and entitled: "Affixation Method and Apparatus for a Disposable Pulse Oximeter Probe".

BACKGROUND OF THE INVENTION

Heretofore the use of pulse oximeter probes has been limited to the use of a costly reusable probe, which is contaminated by use on a patient, or cheaper, single-use probes, which, in the aggregate, amount to a considerable expenditure for a health care institution. The present invention relates to a method of making and affixing a reusable probe to a patient by means of disposable bandage apparatus so that there is no contact between the costly, reusable portion of the probe and the patient. The contaminated bandage apparatus, which is relatively inexpensive, can then be discarded after single patient use and the probe can be re-used with a new bandage apparatus.

Other individuals have attempted to convert single use probes into multi-use probes through a lamination process. In that process, the original adhesive material is removed from the original manufacturer's sensor. The sensor is then laminated in a plastic sheath and the entire sheath is then inserted into a transparent, adhesive-backed sleeve, which is then adhered to a patient. After use, the probe can then be extracted from the sleeve and inserted into a new sleeve for use on another patient.

There are certain disadvantages to this method. Firstly, it is difficult to insert the flexible laminated sensor into a long sleeve. Secondly, the thickness of a laminated sensor inside of a sleeve makes it difficult to bend around, and to stick properly to, a human appendage. Thirdly, transmission and reception of infrared light can be affected by extraneous light entering from the sides of the sleeve. And fourthly, there is some dispute as to the affect on infrared light transmission when passing through the sleeve and the adhesive material coupled thereto.

THE PRESENT INVENTION

The present invention not only solves the problems outlined above, but offers an alternative that is cheap to manufacture and easy to use.

In detail, the present invention is a method for improving the form and affixation method of a reusable pulse oximeter sensor. It comprises a reusable pulse oximeter probe with at least one light emitting diode and one photocell detector wherein said emitter and detector are enclosed in plastic housings, one housing having an aperture aligned with said emitter, and the other housing having an aperture aligned with said detector. Also included is a disposable bandage apparatus which is a generally planar bandage strip having adhesive on at least a portion of at least one face thereof and at least two plastic receptacles attached to the other face thereof, each receptacle having at least one aperture located therein. The probe housings can matedly engage said bandage receptacles and transmit and receive light through the apertures of said mated housings and receptacles, and through the appendage of a patient. The apertures of said receptacles are large enough to accept the tubular protrusions of the housings for the purpose of concentric location and alignment of the housings to the receptacles and the proper transmission and reception of light therethrough. Sandwiched between the adhesive strip and the receptacles attached thereto, are translucent silicone windows for isolation of the reusable probe assembly from the patient. The bandage apparatus may be discarded after single patient use and the reusable probe may be used again on another patient in conjunction with another bandage apparatus. Additionally, the receptacles of the bandage apparatus may have a concave surface on one side thereof in order to seat conformably on a human digit, or they may have a flat surface on at least one side thereof in order to attach conformably to a human foot, nose, or ear. The housings and receptacles also contain "mushroom hook" type hook and loop material for the purpose of adhering and detaching said housings to and from said receptacles. Additionally, the housings and receptacles have recessed areas for adhesion of the "mushroom hook" hook and loop material.

Finally, and in another preferred embodiment, the receptacle of the disposable bandage apparatus may be the mushroom hook material itself which may be attached directly to the planar adhesive strip for the selective engagement of the housings of the probe assembly.

DESCRIPTION OF THE DRAWINGS

The above and other advantages of the invention will become more clear when considered with the following specifications and accompanying drawings wherein.

DESCRIPTION OF THE REUSABLE PULSE OXIMETER SENSOR

Figure 1:
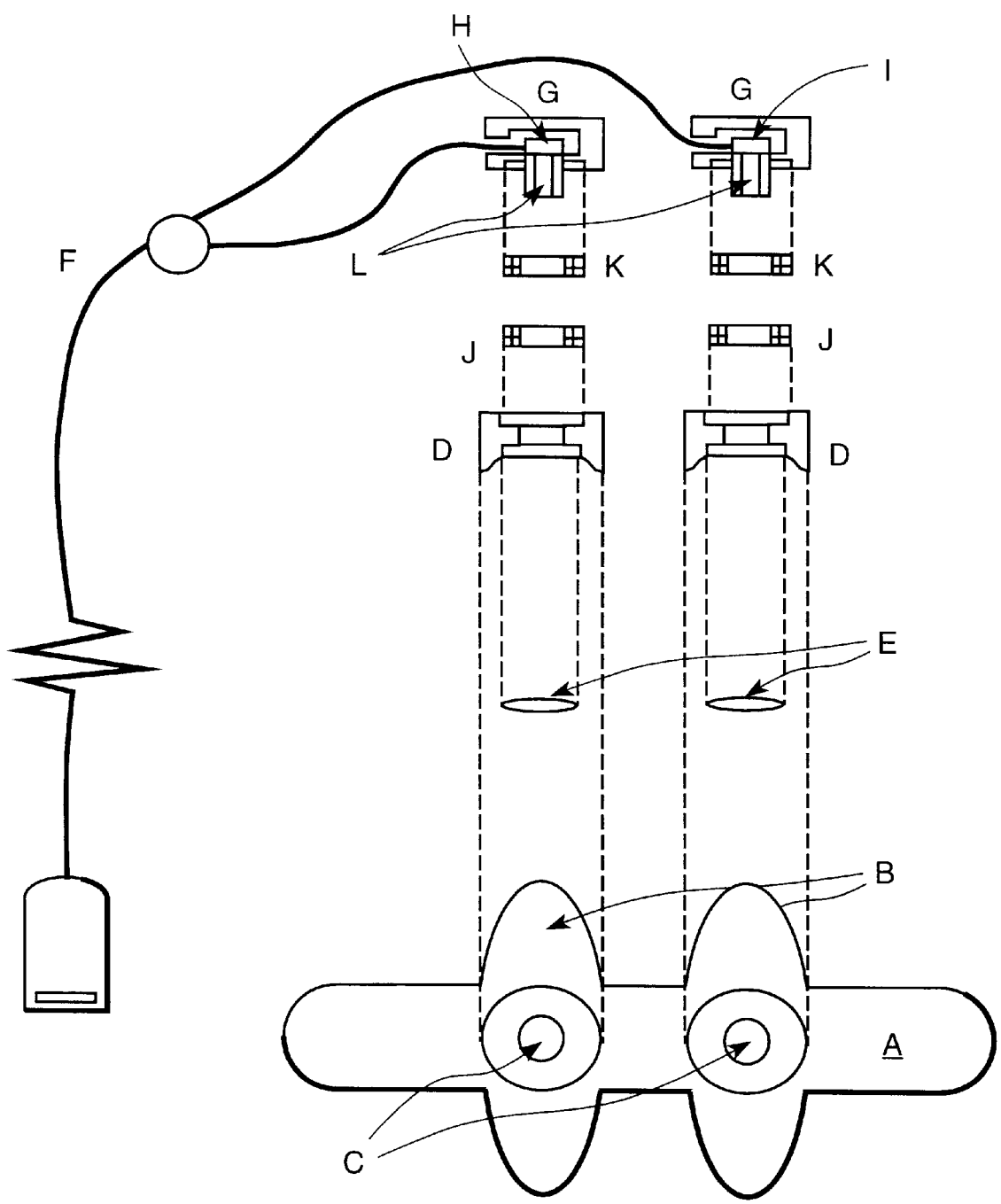
FIG. 1 is an exploded view of the reusable pulse oximeter probe and disposable bandage apparatus incorporating the invention.

The Reusable Pulse Oximeter Sensor constitutes a "Y" style pulse oximeter probe shown as, FIG. 1, Item F. Said probe incorporates two plastic housings shown as FIG. 1, Items G, said housings containing apertures therein, said apertures shown as FIG. 1, Items L. One housing contains the light emitting diode of the probe, FIG. 1, item H, and the other contains the photocell detector, FIG. 1, Item I. The emitter and detectors are aligned with the apertures of said housings in order to transmit and receive light through the human appendage.

Seated within a recessed area of each housing, and attached permanently thereto, is a "mushroom hook" adhesive-backed pad, FIG. 1, Item K. The purpose of these pads is to selectively engage the "mushroom hook" pads, FIG. 1, Items J, attached permanently to the plastic discs, FIG. 1, Items D, and to attach the reusable probe assembly to the Disposable Bandage Apparatus. The Reusable Pulse Oximeter Sensor is shown assembled as FIG. 2, Item A.

Description of the Disposable Bandage Apparatus

The components of the apparatus include a planar, adhesive-backed, strip, shown as FIG. 1, item A, said strip incorporating two oval protrusions centered thereon and shown as FIG. 1, Item B. Said strip also incorporates two apertures, centrally located within said oval protrusions, FIG. 1, Item C, each aperture having a diameter sufficient in size to accommodate the transmission and reception of light from a light emitting diode and photocell detector of a pulse oximeter probe.

On top of said apertures are seated two plastic discs, FIG. 1, Item D, each having a concave base designed to conform to the radius of a human digit, and an aperture of slightly larger diameter than the apertures in the adhesive backed planar strip. Said plastic discs are affixed to the adhesive planar strip by means of a permanent adhesive.

Seated in a recessed area on top of each plastic disc is a "mushroom hook", adhesive backed pad shown as FIG. 1, Item J. The purpose of the "mushroom hook" pads is to selectively engage the "mushroom hook" pads attached to the probe, FIG. 1, Items K, and to attach the probe to the disposable bandage apparatus.

Sandwiched between the two plastic discs and the planar adhesive strip are two translucent silicone windows, FIG. 1, Item E. Said windows are designed to permit the passage of infrared light and yet prevent contact between probe and patient, and consequently, contamination of the reusable probe itself.

Figure 2:
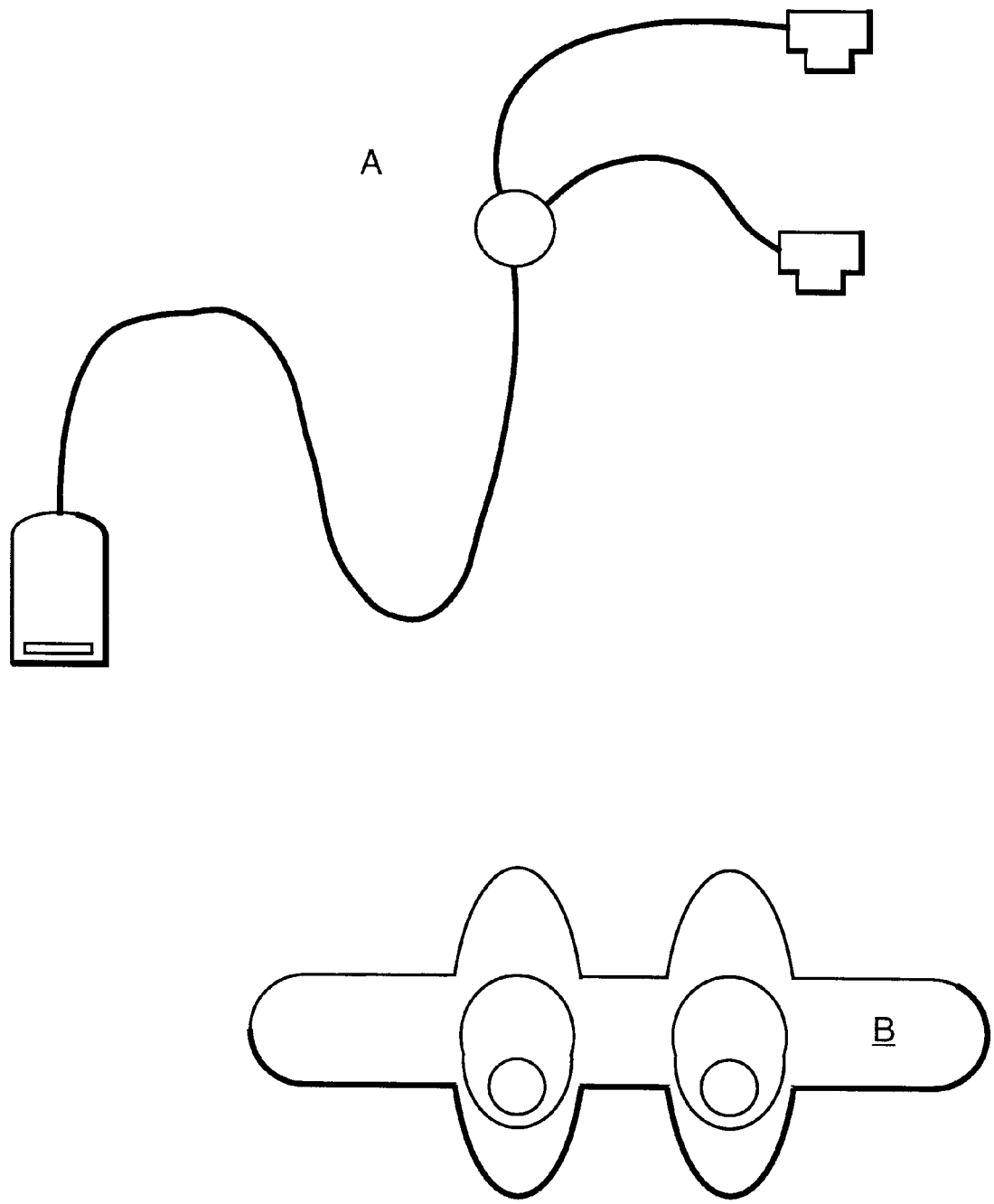
FIG. 2 is a view of the reusable pulse oximeter probe and disposable bandage apparatus shown individually as components of the invention.

The above items constitute the Disposable Bandage Apparatus of the invention, said apparatus being shown assembled as FIG. 2, Item B.

Figure 4:
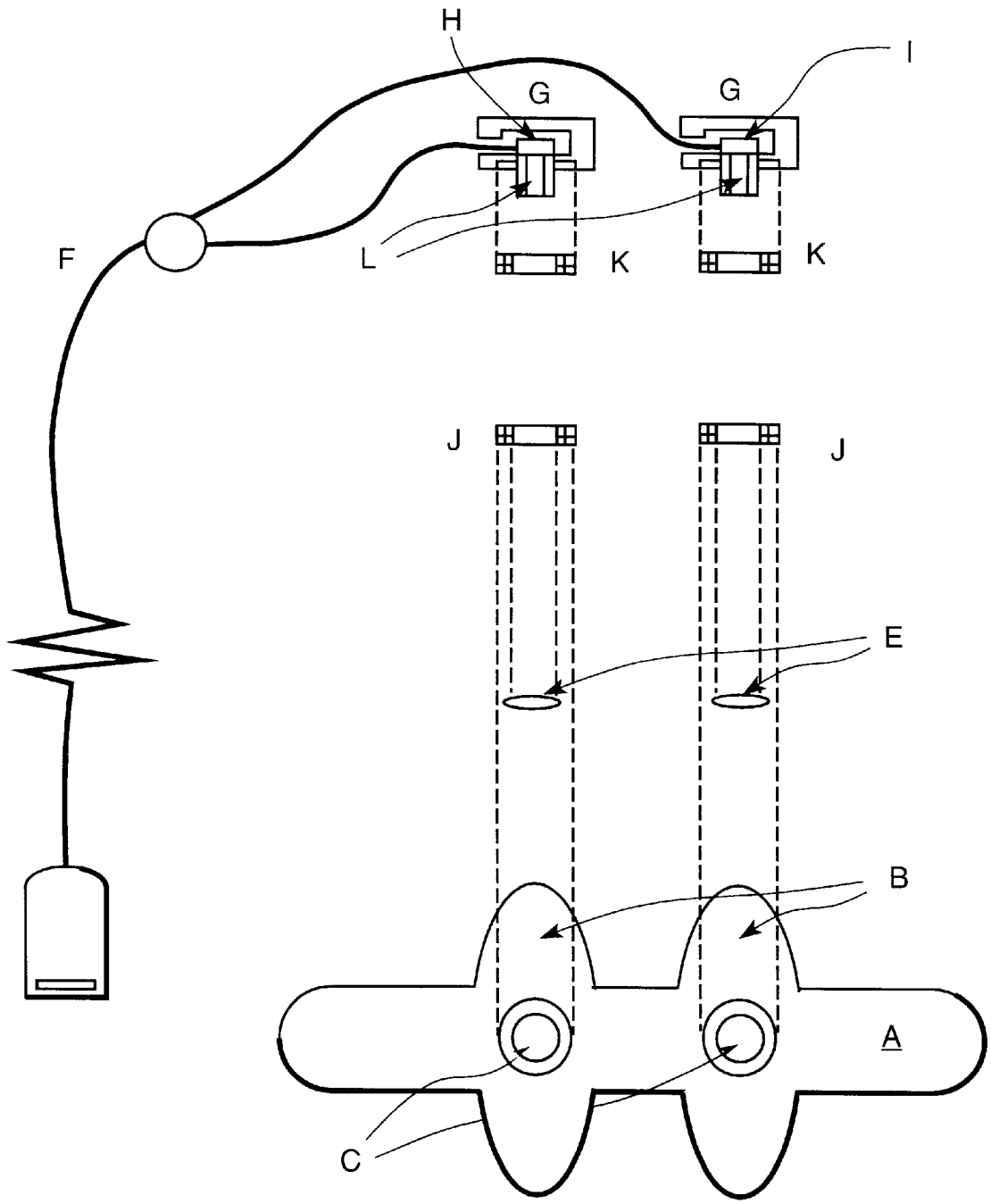
FIG. 4 illustrates an exploded view of another preferred embodiment of the invention in which the "mushroom hook" material itself is used as the receptacle of the disposable bandage apparatus.

In another preferred embodiment of the invention, the Disposable Bandage Apparatus may be configured as in FIG. 4 of the drawings. In that drawing there is an exploded view of the apparatus in which the "mushroom hook" pads of the bandage apparatus, FIG. 4, Items J, are bonded directly to the adhesive planar strip, FIG. 4, Item A, for the selective engagement of the "mushroom hook" pads of the probe, FIG. 4, Items K, said pads being attached permanently to the housings of the probe, FIG. 4, Items G.

Other Fastening Means

As can be appreciated there are many ways of fabricating the above components of the invention. The above description describes attachment of the Reusable Pulse Oximeter Sensor to the Disposable Bandage Apparatus by way of a "mushroom hook" type hook and loop material. In addition to this means a number of other methods may be used including, standard hook and loop material, telephone type modular connectors, "ring and groove" type snap on connectors, "push and twist" type Luerlock connectors, and threaded flange type connectors.

Method of Use

Figure 3:
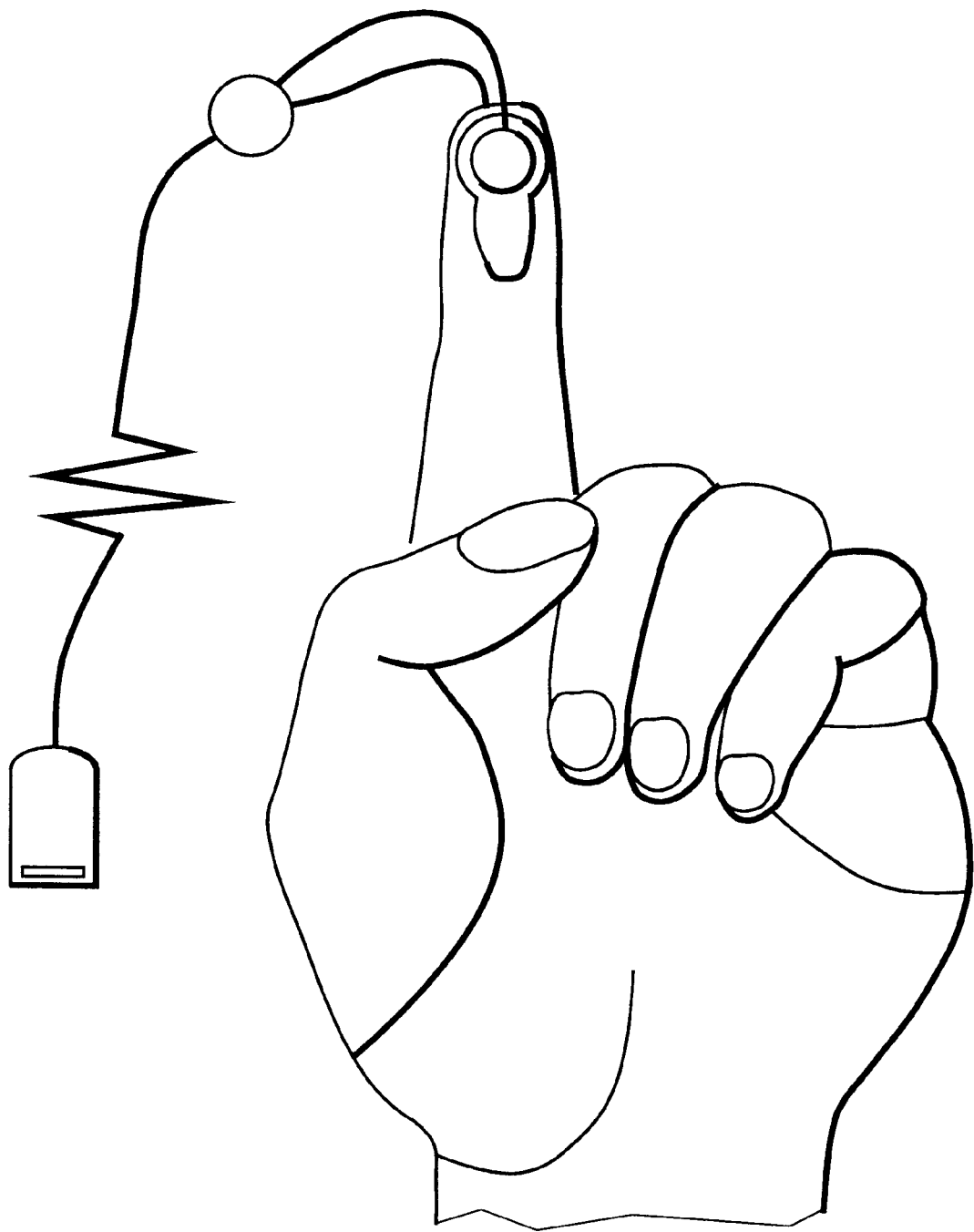
FIG. 3 illustrates the invention in use on a human finger or digit.

For use on each individual patient, the probe is affixed in the following manner:

Firstly, the backing is removed from the adhesive strip of the Disposable Bandage Apparatus. One of the apertures of the apparatus is visually positioned on the center of the nail bed of the patient's appendage and one side of the adhesive strip and the oval protrusions are adhered to the patients digit. The rest of the strip is then looped over the end of the patient's appendage, and the plastic disc is aligned so as to exactly oppose the plastic disc already attached to the other side of the digit. Once the Disposable Bandage Apparatus has been properly adhered to the patient, the plastic housings of the probe assembly can be easily snapped into place on opposing sides of the digit. The entire assembled probe is shown as it would appear in use on a patient in FIG. 3.

When the probe is no longer required on the patient, the housings of the Reusable Probe are simply unsnapped from the Disposable Bandage Apparatus, the bandage apparatus is thrown away, and the probe can then be reused on a new patient in conjunction with a new bandage apparatus.

Advantages of the Present Invention

Current reusable pulse oximeter probes are either "Clam Shell" type clamping devices which can restrict circulation or "Y" type probes which are taped directly to the patient. Both types also come in direct contact with the patient's skin and bodily fluids and need sterilization after use. Because of the fact that these devices incorporate many surfaces and at times, porous materials, proper sterilization is very difficult. With the present invention there is no contact between the reusable probe and the skin or bodily fluids of the patient.

Disposable probes are very costly because of the fact that the cable, connectors and photodiodes are all disposed of after use. The present invention accomplishes the same goals as a disposable probe from a cleanliness standpoint, but since only the attachment apparatus is discarded after use, the cost is much less to a healthcare institution.

The present invention, with the concave shape of the plastic discs of the bandage apparatus, when backed by the adhesive strip, is extremely effective in preventing the entrance of extraneous light from the sides of the patient's digit. Current probes on the market, whether disposable or reusable, because of the nature of their shape and affixation means, have problems in dealing with extraneous light reception.

The present inventions utilizes an easy snap on, snap off, attachment means for attaching the probe to the Disposable Bandage Apparatus. Probe-Shield type devices available in the past not only required the modification of the original manufacturer's probe, but required the difficult procedure of inserting a flexible laminated probe into a sheath for each patient.

Probe-Shield devices, because of the lamination process involved, raised some concern over the transmission and reception of infrared light through the laminating material. The present invention uses a silicone window for the isolation of the probe from the patient. Infrared light transmission and reception is not affected by passage through translucent silicone.

What is claimed is:

1. A reusable pulse oximeter sensor and disposable bandage apparatus, comprising:
   a) a reusable pulse oximeter probe assembly with at least one light emitting diode and one photocell detector wherein said detector and emitter are enclosed in plastic housings, a first of said housings having an aperture aligned with said emitter and a second of said housings having an aperture aligned with said detector;
   b) a generally planar bandage strip having adhesive on at least a portion of at least one face thereof and at least two plastic receptacles attached to the other face thereof, each receptacle having at least one aperture located therein;

wherein said first and second housings can matedly engage said bandage receptacles, and transmit and receive light through the apertures of said housings and receptacles, and through the appendage of a patient.

2. The reusable pulse oximeter sensor and disposable bandage of claim 1 wherein translucent silicone windows are sandwiched between said adhesive strip, and said receptacles attached thereto.

3. The reusable pulse oximeter sensor and disposable bandage of claim 1 wherein there are tubular protrusions on said housing and the apertures of said receptacles are large enough to accept the tubular protrusions of said housings for the purpose of concentric location of the housings to the receptacles and the proper transmission of light therethrough.

4. The reusable pulse oximeter sensor and disposable bandage of claim 1 wherein said bandage apparatus is constructed of inexpensive materials such that it may be discarded after single patient use and said reusable pulse oximeter probe may be used again on another patient in conjunction with a new planar bandage strip.

5. The reusable pulse oximeter sensor and disposable bandage of claim 1 wherein said receptacles have a concave shape on one side thereof in order to seat conformably on a human digit.

6. The reusable pulse oximeter sensor and disposable bandage of claim 1 wherein said receptacles have a flat surface on at least one side thereof in order to seat conformably on a human ear, nose, or foot.

7. The reusable pulse oximeter sensor and disposable bandage of claim 1 wherein the housings and receptacles contain "mushroom hook" type hook and loop material for the purpose of adhering and detaching said housings to and from said receptacles.

8. The reusable pulse oximeter sensor and disposable bandage of claim 7 wherein the housings and receptacles have recessed areas for adhesion of the "mushroom hook" hook and loop material.

9. The reusable pulse oximeter sensor and bandage of claim 1 wherein the receptacles of said disposable bandage are the "mushroom hook" material itself.

10. A method for improving the affixation of a reusable pulse oximeter sensor probe to a patient comprising, providing a planar adhesive strip with at least two apertures therein, and plastic receptacles mounted on top of said apertures and reusable probe components receivable in said receptacles, visually aligning said strip on the digit of a patient by looking through said first aperture in order to attach said first aperture over the nail bed of a patient, and then engaging the reusable probe components in said receptacles.

* * * * *